(12) United States Patent
Joshi et al.

(10) Patent No.: US 6,923,383 B1
(45) Date of Patent: Aug. 2, 2005

(54) CONTROLLED RELEASE OF SUBSTANCES

(75) Inventors: Ashok V. Joshi, Salt Lake City, UT (US); John J. McEvoy, Sandy, UT (US); Truman C. Wold, Salt Lake City, UT (US); Joseph J. Hartvigsen, Kaysville, UT (US); Daniel Earl Snyder, Indianapolis, IN (US); Joseph Raymond Winkle, Indianapolis, IN (US); James Web Kassebaum, Indianapolis, IN (US)

(73) Assignee: Microlin, L.C., Salt Lake City, UT (US)

( * ) Notice: Subject to any disclaimer, the term of this patent is extended or adjusted under 35 U.S.C. 154(b) by 312 days.

(21) Appl. No.: 09/645,673

(22) Filed: Aug. 24, 2000

(51) Int. Cl.[7] ............................................... A62C 13/62

(52) U.S. Cl. ..................... 239/302; 239/340; 239/345; 239/373; 239/327; 239/34; 239/43

(58) Field of Search ..................... 239/34–60, 302–379

(56) References Cited

U.S. PATENT DOCUMENTS

| | | | | |
|---|---|---|---|---|
| 3,679,132 A | * | 7/1972 | Vehe et al. | 239/102.2 |
| 4,175,704 A | * | 11/1979 | Cohen | 239/320 |
| 4,312,347 A | * | 1/1982 | Magoon et al. | 128/260 |
| 4,414,037 A | * | 11/1983 | Friedheim | 134/35 |
| 4,697,549 A | * | 10/1987 | Hair | 119/156 |
| 4,886,514 A | * | 12/1989 | Maget | 604/891.1 |
| 4,968,456 A | * | 11/1990 | Muderlak et al. | 261/30 |
| 5,196,002 A | * | 3/1993 | Hanover et al. | 604/891.1 |
| 5,373,581 A | * | 12/1994 | Smith | 392/390 |
| 5,429,271 A | * | 7/1995 | Porter | 222/3 |
| 5,431,919 A | * | 7/1995 | Maruyama et al. | 424/473 |
| 5,549,247 A | * | 8/1996 | Rossman et al. | 239/57 |
| 5,700,245 A | * | 12/1997 | Sancoff et al. | 222/399 |
| 5,899,381 A | * | 5/1999 | Gordon et al. | 239/34 |
| 5,932,204 A | * | 8/1999 | Joshi | 424/76.1 |

* cited by examiner

Primary Examiner—Dinh Q. Nguyen
(74) Attorney, Agent, or Firm—Factor & Lake

(57) ABSTRACT

The present invention is directed to a device for releasing a fluid. The device includes a housing having an interior region, a fluid contained within the interior region, and the ability to controllably release the fluid from the housing.

79 Claims, 7 Drawing Sheets

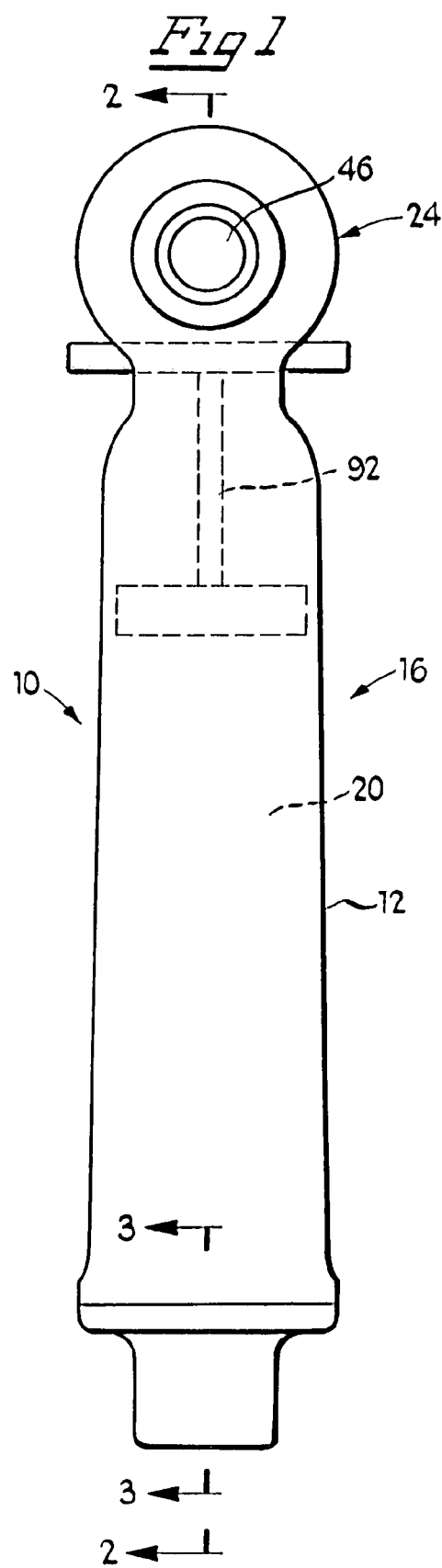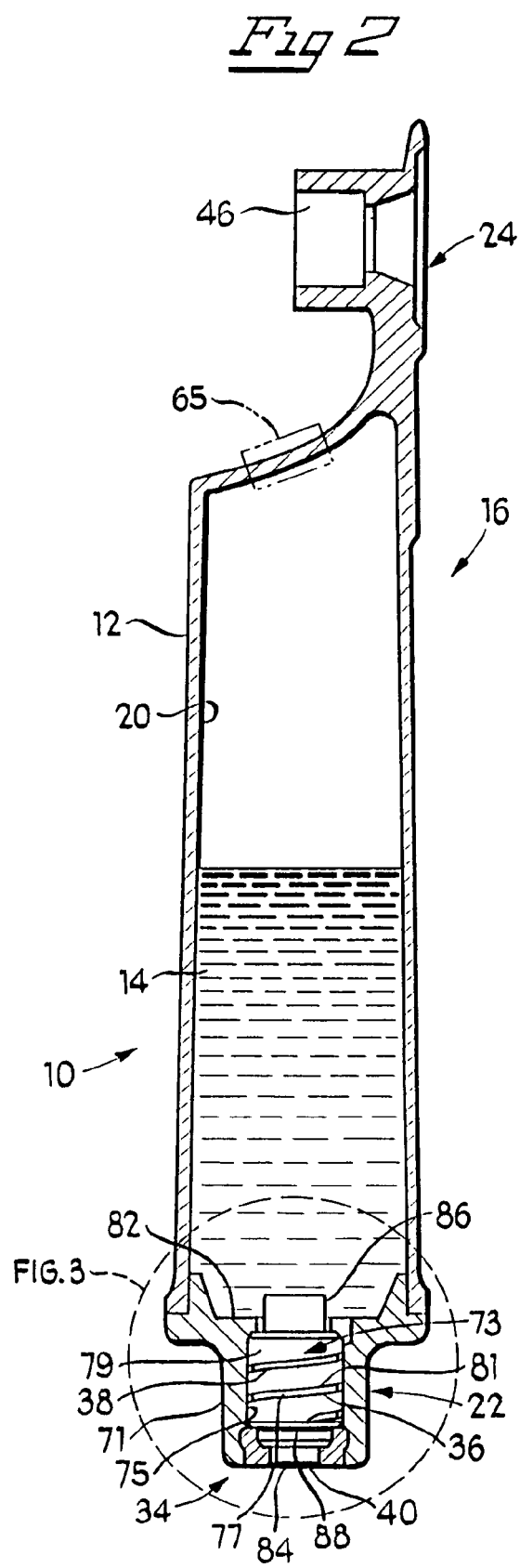

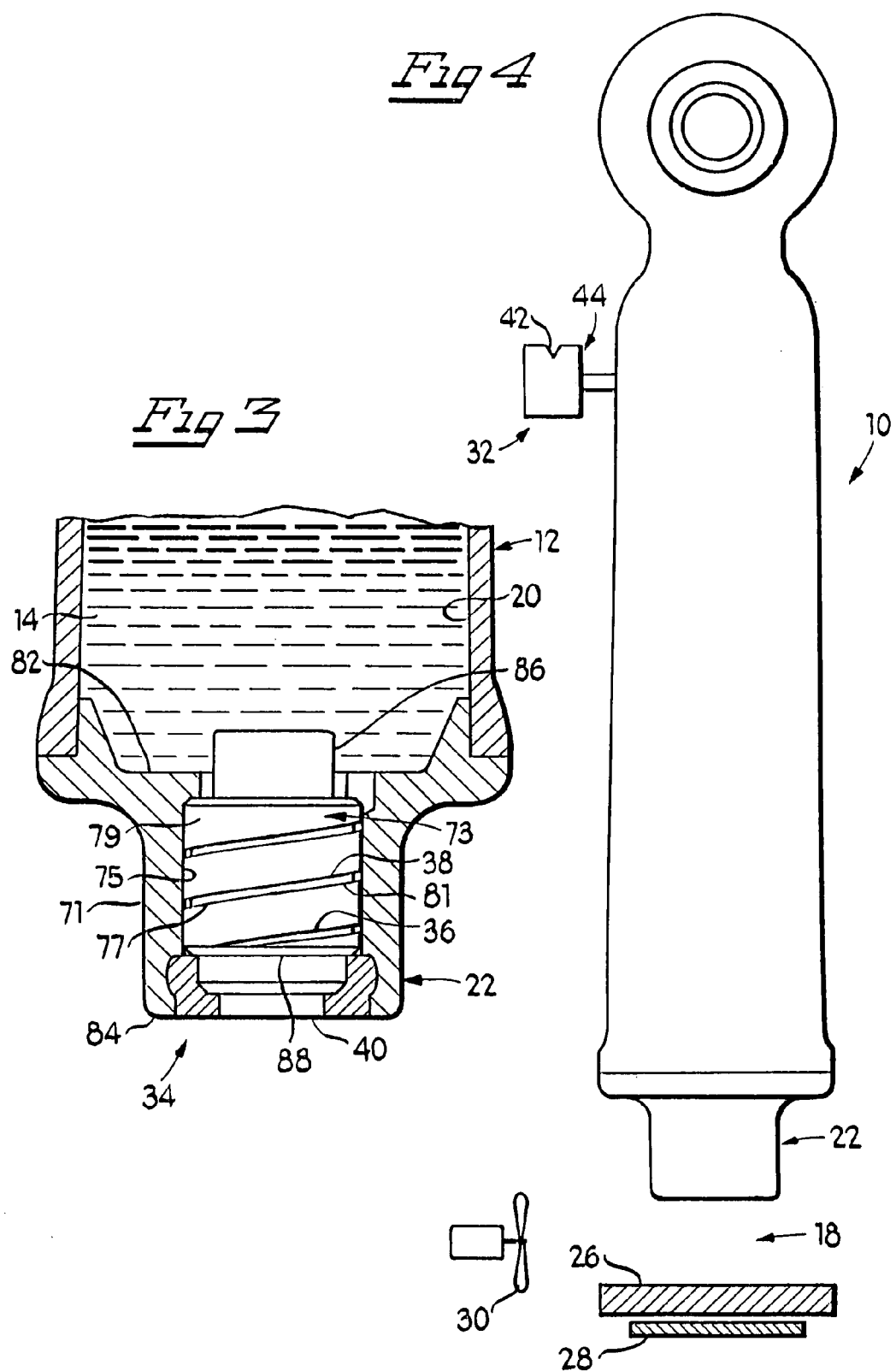

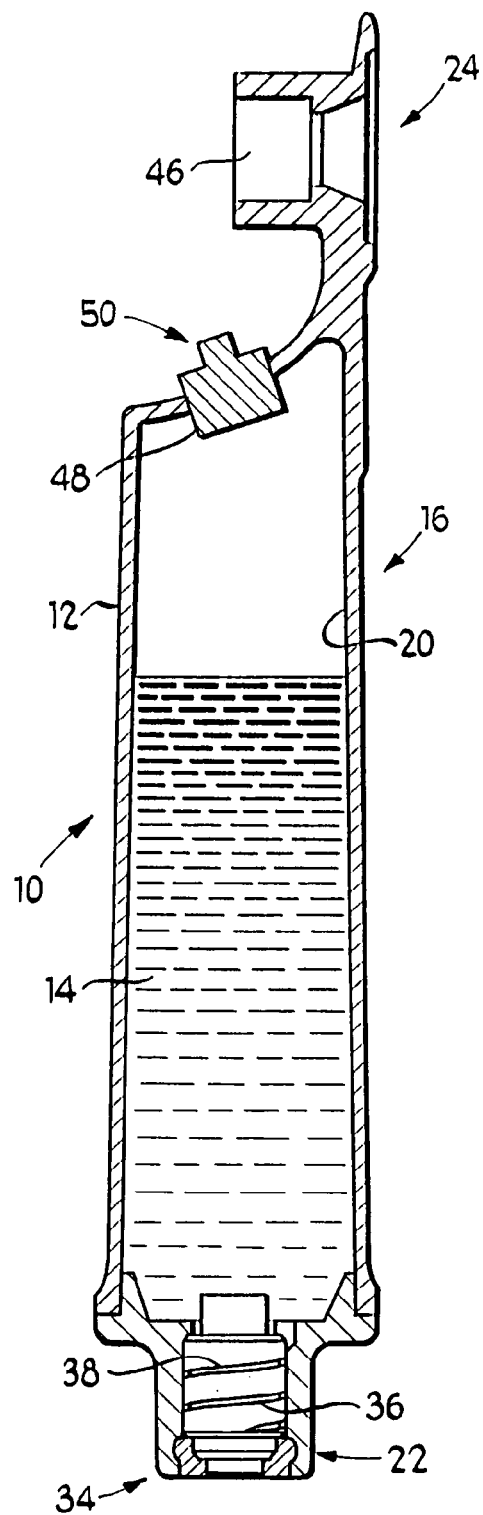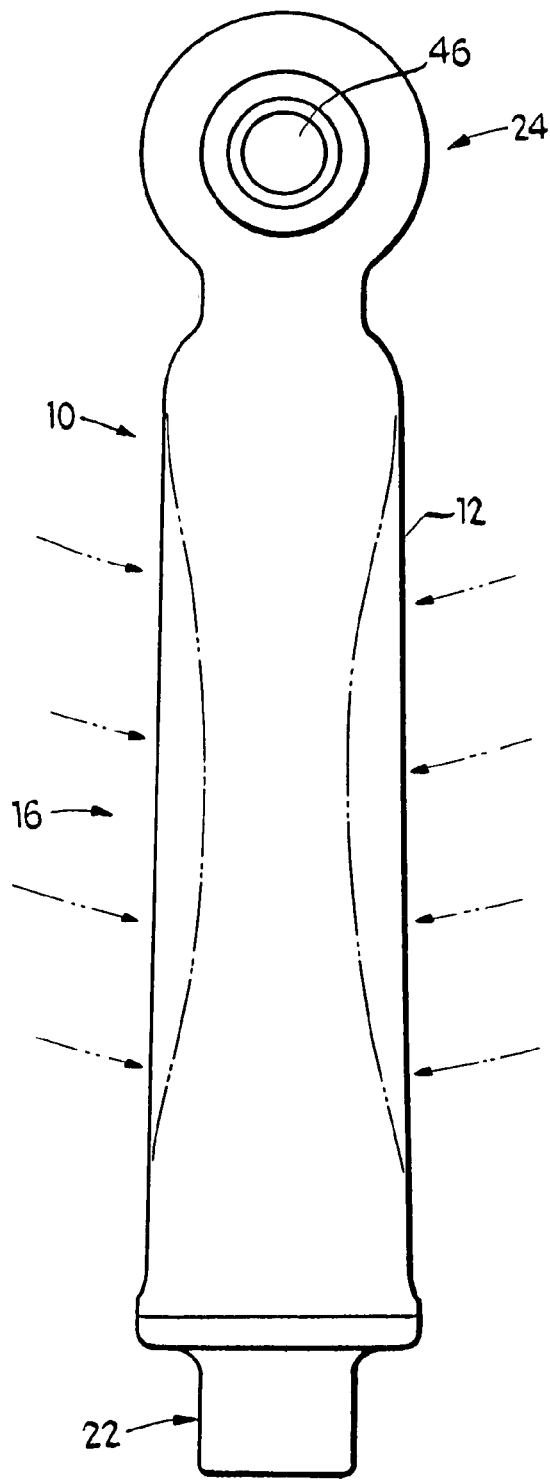

CONTROLLED RELEASE OF SUBSTANCES

BACKGROUND OF THE INVENTION

1. Field of the Invention

The present invention relates in general to the release of fluids and, more particularly, to a device for controllably releasing fluids to the surrounding environment.

2. Background Art

Devices for delivering fluid from a container to the environment, have been known in the art for several years. In particular, many of these devices make use of the principle of diffusion. For instance, some devices make use of a wick based system. In these systems, one end of a wick is placed in a fluid to be dispensed, while the other end is exposed to the atmosphere. Capillary action forces liquid through the wick and up to the exposed end, where the liquid evaporates off of the end of the wick and into the surrounding atmosphere or is wiped off by mechanical means.

Other devices make use of a gravity driven mechanism, allowing liquids to diffuse through a membrane under the force of gravity. Under the force of gravity, the liquid diffuses through the membrane and volatilizes into the surrounding atmosphere from the exposed surface of the membrane.

Although these and other conventional controlled delivery systems have worked well, they have failed to provide for both the controlled and constant (i.e. substantially linear) release of fluids over an extended period of time and the ability to utilize the delivery systems in rugged or more extreme situations. Moreover, it has been difficult to utilize non-volatile liquids, liquids of higher viscosity and gels.

SUMMARY OF THE INVENTION

The present invention is directed to a device for delivering a fluid. The device comprises a housing having an interior, an opening, a gas head space and quantity of fluid within the housing. The device also includes means for causing a pressure difference between the interior of the housing and the immediate surroundings of the housing, wherein the pressure difference forces a predetermined quantity of fluid from within the housing to the opening. Additionally, means are associated with the opening for controlling the flow of fluid therethrough.

In a preferred embodiment of the invention, the pressure differential causing means comprises means for increasing the temperature within the housing which, in turn, increases the pressure of the gas within the housing. The pressure differential causing means may likewise comprise means for lowering the temperature within the housing, to, in turn, decrease the pressure of the gas within the housing.

In another preferred embodiment, the pressure differential causing means may comprise means for increasing or decreasing the barometric pressure external to the housing.

In another preferred embodiment of the invention, the pressure differential means comprises means for pressuring the interior of the housing. The pressurizing means may comprise a gas generating cell, which can be activated by various means.

In yet another preferred embodiment of the invention, the pressure differential causing means may further include means for cyclically varying the pressure differential between the interior of the housing and the immediate surroundings of the housing.

In still another preferred embodiment, the pressure differential causing means may include a check valve, to, in turn, prevent inadvertent flow of fluid when the pressure differential exceeds a predetermined value. It is also contemplated that the flow control means comprise a porous plug.

In another preferred embodiment, the flow control means may include a tunnel of predetermined length and cross-sectional area, so as to permit a certain level of maximum flow therethrough. In one such embodiment, the tunnel may comprise a tortuous path such as a helical configuration, although other configurations, such as sinusoidal paths are likewise contemplated.

In one preferred embodiment of the invention, the device further comprises an emanator associated with the opening of the housing. The emanator may be positioned a predetermined distance from the opening of the housing and can be constructed of a porous-type material. It is also contemplated that the emanator includes a non-porous surface.

In such a preferred embodiment, the emanator may include means for enhancing the volatilization of fluid which is volatile. Such enhancing means may comprise a ventilation fan associated with the emanator, a heating element or ultrasonic energy, among other things.

In another preferred embodiment, the invention further includes means for providing a bolus to, in turn, temporarily increase the quantity of fluid delivered from the device. The bolus providing means may comprise means for increasing the pressure within the housing so as to increase the flow of fluid through the opening. The bolus may include a second opening associated with the housing, as well as means for delivering the fluid within the housing through the opening.

In such a preferred embodiment, it is contemplated that the delivering means comprises a spray pump or an atomizer.

In still another preferred embodiment of the invention, the device includes means for attachment to a living being, such as to the ear of an animal, or to the wall or window of a vessel, among other attachment environments.

In another preferred embodiment of the invention, the housing includes means for releasing a predetermined quantity of fluid therefrom. In such an embodiment, the predetermined release means includes a fixed volume gas chamber, a fixed volume fluid chamber having a fluid release opening, and separating means between the fixed volume fluid chamber and the fixed volume gas chamber. The separating means may comprise a flexible diaphragm which, upon increased expansion of the gas in the fixed volume gas chamber, is forced against the fluid.

In such a preferred embodiment, the housing may include a first fluid control valve (check valve) operatively associated with the fluid release opening. The device may further include a fluid reservoir which is operatively connected with the fixed volume fluid chamber. The fixed volume fluid chamber may include a second fluid control valve (check valve) operatively associated with the fluid reservoir.

The present invention is also directed to a method of delivering a fluid comprising the steps of a) providing a fluid within a housing; b) providing an opening in fluid communication with the surroundings of the housing and with the fluid; c) causing a pressure difference between the housing and the surroundings of the housing; and d) utilizing the pressure difference to direct fluid through the opening.

The invention further comprises a restrictive opening for controlling the passage of fluid therethrough. The restrictive opening comprises a restrictor plug, a receptacle and a groove. The restrictor plug includes an outer surface, a first end and a second end. The receptacle includes an inner surface, a first end and a second end. The groove is disposed on one of the inner and outer surfaces extending from the first end to the second end thereof. A tunnel is defined by the cooperation of the groove and the outer surface as a result of the positioning of the restrictor plug and the receptacle into operative engagement. The tunnel permits the passage of fluid from the first end to the second end of the restrictor plug in a controlled manner.

In a preferred embodiment, the groove is disposed on the outer surface of the restrictor plug. In another preferred embodiment, the groove extends circumferentially about the outer surface of the restrictor plug. In yet another preferred embodiment, the groove extends longitudinally along the outer surface of the restrictor plug in a sinusoidal configuration.

Preferably, the groove comprises a first groove and a second groove. The first groove is disposed on the outer surface of the restrictor plug. The second groove is disposed on the inner surface of the receptacle. The tunnel is defined by the placement of the first and second groove in fluid communication upon positioning of the receptacle and the restrictor plug into operative engagement.

In such a preferred embodiment, one of an effective length and an effective area of the tunnel can be varied by relative movement of the restrictor plug and the receptacle, and, in turn, the first and second groove.

In another aspect of the invention, the invention comprises a device for delivering fluid. The device includes a housing having an interior region and an opening. A quantity of fluid is disposed within the interior of the housing. Means are associated with the opening for controlling the flow of fluid through the opening at a substantially constant rate.

In another aspect of the invention, the invention comprises a housing having a quantity of fluid within its interior. The fluid includes an effective dose. Means are associated with an opening of the housing for controlling the flow of fluid to a rate substantially corresponding to the effective dose of the fluid.

In another aspect of the invention, the invention comprises a device for delivering a fluid. In such an embodiment, means are associated with the opening for precluding the development of resistance to the parasiticide.

BRIEF DESCRIPTION OF THE DRAWINGS

FIG. 1 is a side elevational view of a first embodiment having controlled substance release device means;

FIG. 2 is a cross-sectional view of the first embodiment taken about lines 2—2 of FIG. 1;

FIG. 3 is a partial cross-sectional view of the first embodiment taken about lines 3—3 of FIG. 1;

FIG. 4 is a side elevational view of a second embodiment of the controlled substance release device;

FIG. 5 is a side elevational view of a third embodiment of the controlled substance release device;

FIG. 6 is a side elevational view of a fourth embodiment of the controlled substance release device;

FIG. 7(b) is a graph of oven temperature cycle used to generate the data in the graph of FIG. 7a;

DETAILED DESCRIPTION OF THE DRAWINGS

Figure 7A:
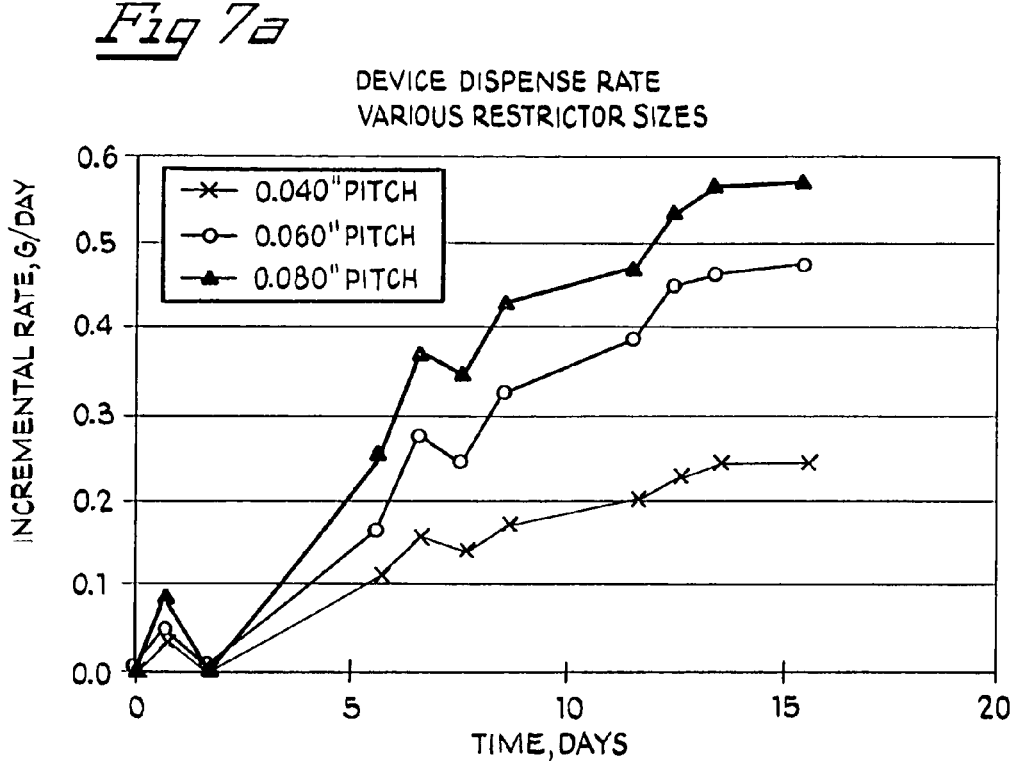
FIG. 7(a) is a performance graph of experimental test data for quantity of fluid dispensed through tunnels of various pitch over a period of time.
Figure 7B:
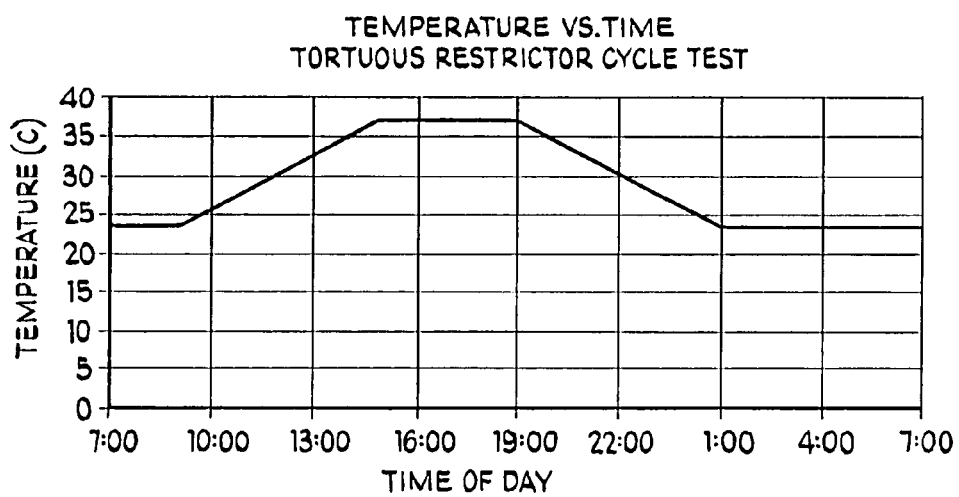

While this invention is susceptible of embodiment in many different forms, there is shown in the drawings and will herein be described in detail, several specific embodiments with the understanding that the present disclosure is to be considered as an exemplification of the principles of the invention and is not intended to limit the invention to the embodiments so illustrated.

Control substance release device 10 is shown in FIGS. 1 and 2 as comprising housing 12, fluid 14 and means 16 for causing a pressure differential and possibly means for enhancing delivery. As will be explained in detail, device 10 can be utilized in various environments, such as in association with the release of a fluid (i.e. parasiticide which is a chemical or biological agent or other means for controlling, killing or reducing the population of any life cycle stage of insects, acarines and other parasites that infest or infect vertebrate animals and their surroundings) to the skin of a living being, such as a human or an animal, as well as in association with release of a fluid (i.e. fragrance) in the cabin of an airplane, an airplane lavatory or elsewhere in an airplane body. Indeed, these are examples only and the invention is not limited to any particular environment, field of use fluid.

Housing 12 is shown in FIG. 2 as including interior region 20 which retains the desired fluid, opening 22 which is in fluid communication with the surroundings outside of the housing and means 24 for attaching the housing to another object. Housing 12 generally comprises a natural or synthetic plastic material, however, other materials, such as glass, metals and alloys thereof are likewise contemplated for use. Certain materials may be selected based on their heat retention, absorption and dissipation characteristics. Generally, it is preferred that the housing be substantially rigid so that the variations in the pressure do not expand or contract the housing, and, in turn, the interior region. However, as will be explained below, in certain embodiments, it is advantageous to alter the volume of interior region 20.

It is contemplated that interior region 20 includes a volume of about 10–15 cm$^3$. However, it will be understood that the interior region is not limited to any particular size nor to a particular range of sizes. As will be explained below, the interior region is utilized for the storage of both air and another fluid. The fluid contemplated for use in association with the present invention may comprise, for example, any one of perfumes, parasiticides, insect repellants, air fragrances, medicines, greases and pastes and combinations thereof, in liquid and/or gel form and in varying viscosities. In certain embodiments, the housing may be provided pre-filled with a fluid for a single use. In other embodiments, the housing may include a refilling port which will enable a user to refill and reuse the device.

Regardless of the type of fluid utilized, the interior region likewise includes an initial quantity of air (or other gas). As will be explained, the pressure differential causing means acts upon this quantity of air to, in turn, drive fluid from within the interior region, or to facilitate the entry of gas from ambient. The initial quantity of air that is supplied in the interior region can be varied to achieve various initial delivery rates until the linear dispensing is reached. Specifically, the greater the initial volume of air, the quicker the device reaches the desired delivery rate.

Opening 22 is shown in FIGS. 2 and 3 as comprising receptacle 71, restrictor plug 73, retaining member 93, and means 34 for controlling the flow of fluid. Receptacle 71 includes inner surface 75, first end 82 and second end 84. In one embodiment, opening 22 and housing 12 comprise a material which facilitates assembly by way of ultrasonic welding of the opening to the lower end of housing 12. Restrictor plug 73 includes first end 86, second end 88 and groove 77 in outer surface 79. As such, when restrictor plug is positioned within receptacle 71, and inner surface 75 is in abutment with outer surface 79, tunnel 81 is defined by groove 77 in cooperation with inner surface 75 and outer surface 79. In turn, the groove essentially provides the means for controlling the fluid flow through the opening. As will be understood, retaining member 93 comprises a snap ring which cooperates with a corresponding recess positioned on inner surface 75 of receptacle 71, to, in turn, retain the restrictor plug within the receptacle.

In the embodiment shown, tunnel 81 includes tortuous path 36 (i.e. a path which restricts the free flow of fluid), such as helical passage 38 which extends around outer surface 79 of restrictor plug 73 and includes a cross-sectional area, a volume, a length and a pitch. The tunnel restricts the rate at which the fluid can be released from interior region 20 (i.e. a maximum flow rate). As will be understood, by varying any one or more of the length, cross-sectional area, a volume and/or pitch, different rates of release of the fluid can be achieved. (See the graphs of FIGS. 7*a* and 7*b*). In addition, while a single tunnel is shown, there is no limit on the quantity of tunnels that may be utilized. In another embodiment, the tortuous path may comprise a tunnel having a non undulating, straight path. Such an embodiment may be well suited for fluids having relatively higher viscosities.

The tunnel is not limited to any particular configuration or to extending about the circumference of the outer surface. For example, as shown in FIGS. 9 and 10, groove 77 may comprise two sinusoidal (or other shaped) paths that generally do not extend about the entire circumference of the outer surface of the restrictor plug. In such an embodiment, the length of the tunnel can be varied by varying the amplitude or the frequency of the sinusoid.

In another embodiment, as shown in FIG. 11 it is likewise contemplated that first groove 83 may be disposed on the outer surface of the restrictor plug and second groove 85 may be disposed on the inner surface of the receptacle. In such an embodiment, the first and second grooves are positioned so that they are in fluid communication with each other and so that they cooperate to provide a passage for the fluid. By rotating or longitudinally moving the outer surface of the restrictor plug and the inner surface of the receptacle, the orientation of each groove can be changed relative to the other groove to, in turn, adjust and vary the effective length and cross-sectional area of the resulting tunnel.

Advantageously, since the path of tunnel 81 is relatively lengthy and relatively small in cross-sectional areas, it is difficult to displace the fluid therein at a rate exceeding the pressure of the interior region. Thus, even if the device is shaken or otherwise moved or jarred, the flow of fluid within tunnel 81 is largely unaffected.

Opening 22 may additionally include filter 40 to preclude the passage of undesired debris and contaminants into interior region 20.

In other embodiments, opening 22 may include a membrane (not shown) positioned over the opening to control the permeation of the fluid from interior region 20 of device 10. Such a membrane helps control the pressure within interior region 20 of housing 12, and, in turn, permeation of the fluid, by maintaining a certain vacuum due to the action of gravity thereagainst. Alternatively, and as shown in FIG. 2, the membrane 65 (shown in dashed lines) may be located at the top, controlling the permeation of air out of the headspace.

Attachment means 24, as shown in FIGS. 1 and 2, may comprise a variety of structures for facilitating attachment to an outside surface (i.e. a living being such as an animal). In the embodiment shown, attachment means 24 is integrally formed with housing 12 and includes opening 46 (i.e. the female component) which facilitates the receipt of a fastener (i.e. the male component, such as a rivet), or the like. In an alternate configuration, the male component may be integrally formed with the housing, in which case the female component is fastened thereto. In other embodiments, the attachment means may comprise other structures such as a cord, an adhesive double-stick tape, a hook-loop fastener among others.

As shown in FIG. 4, control substance release device 10 may additionally include volatilization enhancing means 18. The volatilization enhancing means can be associated with opening 22 to further enhance volatilization of the fluid, wherein the fluid comprises a volatile substance. For example, the volatilization enhancing means may comprise emanator pad 26 (comprising a porous material, such as a sponge, paper element and fabric or a non-porous material) which can be positioned to receive the volatile substance as it exits opening 22. Additionally, fans 30, heating element 28 and/or ultrasonic energy, among others, can be associated with emanator pad 26 as a means of enhancing the volatilization of such a fluid. The emanator pad can be positioned at any predetermined distance from the opening.

Volatilization enhancing means 18 may further include means 32 for providing a bolus, to, in turn, temporarily increase the delivery of the volatile fluid from the device. The bolus providing means may comprise a second opening 42 and means 44 for delivering fluid to the second opening. Delivering means 44 may comprise an atomizer or a spray pump which can be activated manually, or, alternatively, can be activated automatically and cyclically upon exposure to a predetermined pressure build up. As an example, such a bolus providing means is particularly applicable for use in association with a device attachable to an animal having parasiticide therein. It is also contemplated that the bolus be used in an embodiment that does not use a volatile fluid. Likewise, the bolus may be used in association with the above-described fans, heating elements and ultrasonic energy.

Pressure differential causing means 16 is shown in FIG. 5 as comprising a variety of means which cause a pressure differential between interior region 20 and the ambient conditions (temperature and barometric pressure) of the immediate surroundings of housing 12. As will be explained, such a pressure difference between these zones forces a predetermined quantity of fluid from within the housing through the opening, and replaces the lost fluid with air from the surroundings.

Figure 7C:
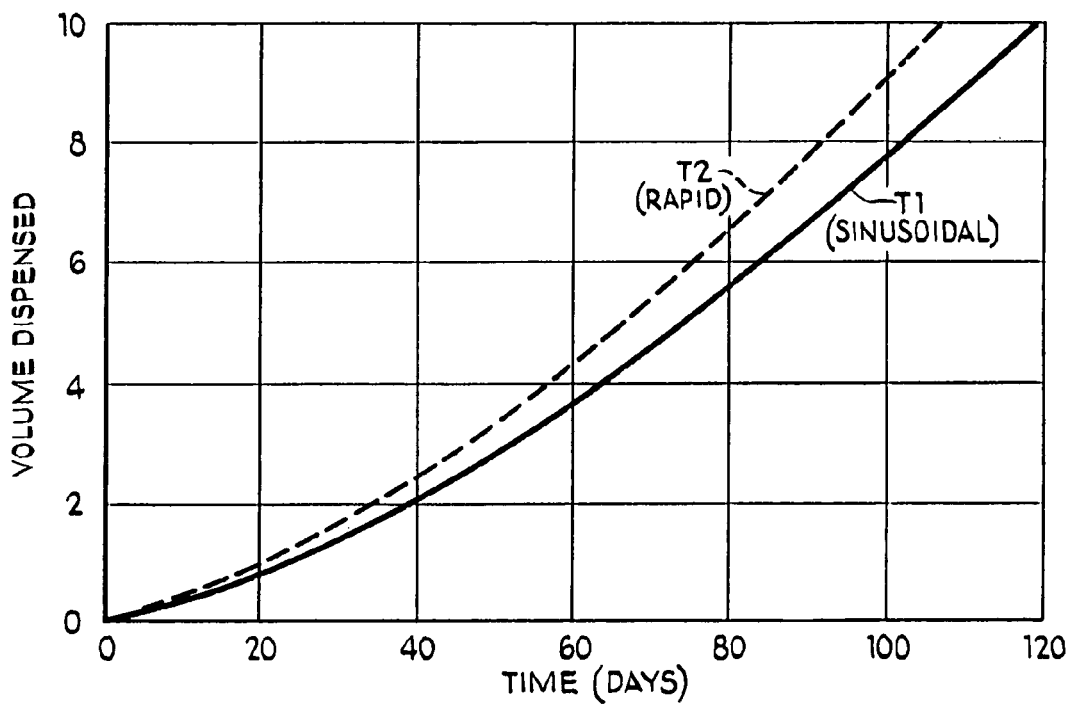
FIG. 7(c) is a theoretical performance calculation of a device in two different temperature cycle profiles.

In one embodiment, the pressure differential causing means may comprise a means for increasing the temperature of interior region 20 of housing 12. (See FIGS. 7c and 7d). Such an embodiment is well suited for use, for example, in association with an animal parasiticide dispenser which may be attached to an animal, such as an ear of a cow. Specifically, as the animal grazes in the open field, housing 12 absorbs heat radiated by the sun, thereby causing an increase in temperature of the interior region 20 as well as the fluid and any other gaseous material therein (air and any vaporized fluid). With respect to the fluid and the gaseous material, an increase in temperature likewise increases the pressure within the interior region of the housing. In turn, the pressure within the housing becomes greater than the barometric pressure of surrounding ambient conditions. The pressure difference forces the fluid toward opening 22 in housing 12. Next, fluid is driven by the internal pressure through tunnel 81 defined by groove 77 to ambient. It is likewise contemplated that in certain embodiments the user may be able to adjust (i.e. decrease or increase) the volume of the interior region so as to increase or decrease the pressure therewithin. For example, housing 12 may include a manually adjustable piston-like configuration 92 (FIG. 1) which enables operative adjustment/altering of the interior volume of the housing.

At the end of the day, or at any time that ambient temperature reduces, the device cools. In turn, the internal gas (i.e. vaporized fluid and air) cools, the pressure is reduced and the gas within the interior region essentially contracts. To compensate for the contraction of the gas remaining in interior region 20, outside air (or other gas) is directed into tunnel 81 defined by groove 77, and in turn, into interior region 20. The next day, or when the ambient temperature again increases the cycle is repeated. The cycle can continue until such time that the fluid is substantially dispensed.

By utilizing a restricted opening (i.e. one with tunnel 81) in cooperation with the pressure differential causing means, the rate of delivery of fluid through opening 22, in either direction, can be closely controlled. In fact, a slow rate of flow in either direction via opening 22 can be achieved, and such a rate can be maintained for an extended period of time (i.e. 120 days or more). More specifically, without any restriction on the opening, the flow through opening 22 is governed by the Ideal Gas Law, i.e. gas volume, pressure and temperature differences only. However, by adding a restricted opening, an additional variable is presented, namely, a maximum flow rate that can be achieved through tunnel 81. By sizing the restricted opening (i.e., the cross-sectional area, pitch, volume and/or the length of the tunnel), varying maximum delivery rates can be achieved. In turn, once the pressure difference causes a maximum flow condition through the opening, further pressure differences may extend the duration of the flow (i.e. a substantially constant flow rate providing a substantially linear dispensing), but will not further increase the flow rate significantly. Thus, a more uniform distribution of flow over a longer time period can be achieved. In addition, since the flow rates will not increase substantially, customization of device 10 for specific geographic regions may not be necessary.

Use of the restricted opening in cooperation with the pressure differential causing means of the present invention is particularly suitable for use in association with an animal ear tag to deliver a parasiticide. Conventional ear tags which generally comprise a molded polymer matrix impregnated with a substance such as a parasiticide have an inconsistent, erratic and incomplete delivery of the substance. Among other delivery problems, these tags release the substance after packaging, wherein the substance crystallizes on the surface of the tag itself, exposing the user to a high concentration of the parasiticde. Further, these tags initially supply excessive doses of the substance and over time reduce the level of delivery until the supply of the substance falls below an effective dose. Exposure to non effective doses causes parasites to develop resistance to the substance. Moreover, such tags are generally limited to certain substances due to solubility and/or compatibility concerns between the substance and the polymer matrix as well as due to molecular weight and size constraints. For example, compounds like ivermectin and spinosad have relatively high molecular weights (>700) and poor solubility in various polymers such as polyethylene which essentially render these compounds unable to be formulated in conventional ear tags.

To the contrary, the present invention provides for a substantially constant delivery rate resulting in a substantially linear delivery of fluid which can be adjusted by altering the above-described properties of tunnel 81. As a result, a proper dose of the fluid can be maintained throughout the life of the device, and until substantially all of the fluid is depleted. In turn, such control of the delivery of fluid essentially provides a means for precluding the development of resistance by parasites by providing consistent, therapeutic levels of the parasiticides.

In addition, since the primary delivery is not through diffusion and is not dependent on high solubility of a parasiticide in a polymer matrix, the fluid utilized in the present invention can be expanded to include previously unusable parasiticides and still include compounds previously dissolved in polymer matrices. These include, but are not limited to various avermectins, benzimidazoles, milbemycins, carbamates, organophosphates, phenylpyrazoles, amidines, insect growth regulators, juvenile hormones, nicotinoids, pyrroles and naturalytes (i.e. the spinosyn family). Representative compounds may include abamectin, doramectin, eprinomectin, selamectin, alphamethrin, amitraz, coumaphos, ivermectin, deltamethrin, cyhalothrin, diazinon, cyromazine, cypermethrin, milbemycin, cyfluthrin, cyloprothrin, famphur, fenthion, fenvalerate, flucythrinate, flumethrin, hexaflumuron, lindane, lufenuron, malathion, methoprene, metriphonate, moxidectin, permethrin, pyrethrin, pyrethrum, phosmet, pirimiphos, chlorvinphos, rotenone, propetamphos, tetrachlorvinphos, zetacypermethrin and spinosad, among others.

Two samples prepared in accordance with the teachings of the present invention were tested. The embodiments which included a spinosad compound (which is generally not usable in association with conventional devices) in a fluid formulation were tested in extreme conditions. The composition of the spinosad compound was as follows: Spinosad @ 90%, 16.7% wt/wt; Isopropyl myristate, 23.2% wt/wt; Oleic acid, 60.0% wt/wt; Antioxidant 0.1% wt/wt. The test comprised the comparison of the quantity of flies contained on three different groups of animals. The first group did not have any parasiticide control device or parasiticide applied thereto. The second and third groups utilized one of the two sample devices prepared in accordance with the present invention. The differences between the embodiments utilized on the second and third groups comprised changes in the properties of the tunnel.

Figure 7D:
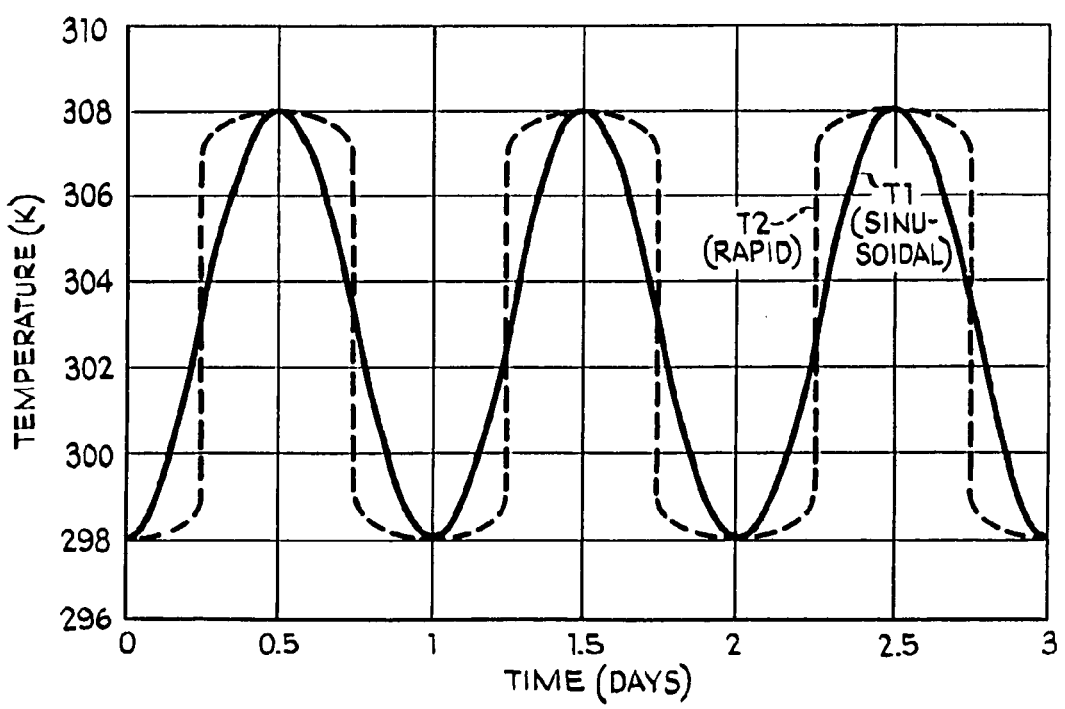
FIG. 7(d) is a graph of the two temperature cycle profiles used to calculate the results of FIG. 7(c)
Figure 7E:
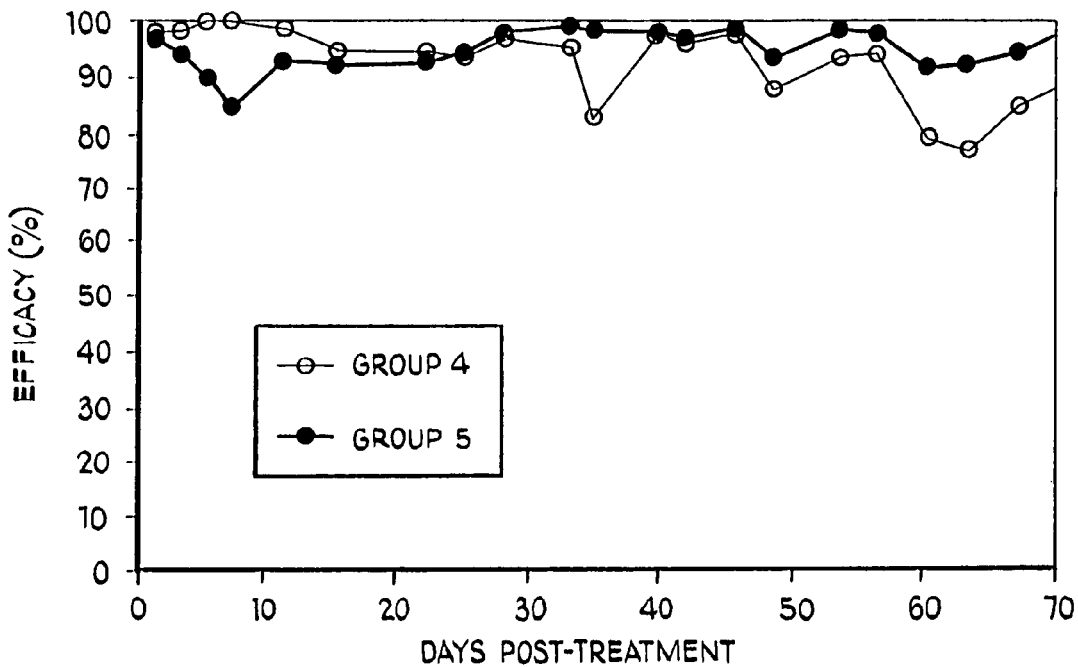
FIG. 7(e) is a graph of test results showing the efficacy of two sample devices prepared in accordance with the present invention over a period of 70 days.

Results were obtained over time wherein efficacy of each of the sample devices was calculated by comparing the quantity of flies on the first group of animals to the quantity of flies on each of the second and third groups. From this, an efficacy ratio was calculated for each of the second and third groups of animals. A graph depicting the results of the test over the first 70 days is shown in FIG. 7(d) wherein "Group 4" represents the second group of animals and "Group 5" represents the third group. As can be seen, each embodiment of the invention maintained an efficacy in excess of 75% (and often in excess of 90%) in these extreme conditions over the first 70 days.

In another embodiment of the invention, the pressure differential causing means may comprise means for decreasing the pressure of the immediate surroundings of the device. Such an embodiment is well suited, for example, in association with a cabin of an airplane, or an airplane lavatory. In particular, as the plane takes off, the cabin pressure decreases an amount which, in turn, creates a pressure difference between interior region 20 of housing 12 and the surrounding ambient air. In turn, the greater pressure within interior region 20 forces the fluid from within the interior region through opening 22 (which may or may not include a restrictor). As the plane lands, the pressure becomes greater in the cabin. As a result, cabin pressure after landing is greater than the pressure within interior region 22, and, in turn, air is directed from ambient surroundings through opening 22 into interior region 22. This cycle is repeated each time the cabin is depressurized until the substance is fully dispensed.

In one such an embodiment, as shown in FIG. 5, the pressure differential causing means may further include gas generating cell 48 (such as a conventional electrochemical gas generating cell, piezoelectric cell or other non-electrochemical gas generating cell). Such a cell generates a gas (pressure) within interior region 20 of housing 12. These cells are useful to generate pressure within interior region 20 to maintain the flow of fluid from the interior region, in, for example, longer flights.

In the embodiment of FIG. 5, the gas generating cell may include means 50 for selectively activating the cell. Wherein the cell comprises an electrochemical gas generating cell, the selective activating means may comprise a manual switch or an automatic switch which is activated upon the sensing of a predetermined condition. A predetermined condition may comprise a predetermined temperature, pressure or the passage of a predetermined period of time, for example.

In another embodiment, shown in FIG. 6, wherein the volume of the interior region of the housing is capable of being altered, the pressure differential causing means comprises means for increasing the pressure of the immediate surroundings of the device. In such an embodiment, housing 12 may be substantially flexible and capable of being compressed by ambient pressure. Alternatively, the interior region may include a plunger or piston slidably movable therein (such as shown in FIG. 1).

In such an embodiment, as the pressure increasing means increases the pressure immediately surrounding the housing, the flexible housing will react to the pressure by reducing the volume (i.e., collapsing) of the interior region thereof. The collapse of the interior region of the housing will, in turn, force the fluid within the interior region of housing toward the opening therein. Such an embodiment is well suited for use in association with the cabin or interior quarters of, for example, a submarine wherein an increase in pressure of the cabin (interior quarters) of the submarine creates a pressure differential between ambient and the pressure within the interior region of the housing. The pressure differential, as explained above, causes compression of the housing and causes the fluidic substance within interior region 20 of housing 12 to be dispensed through the opening in the housing (which may or may not include flow control means 34). This will continue until the pressure within the housing and the pressure surrounding the housing is equalized.

As the submarine returns to the surface, the pressure in the cabin is reduced, thereby returning the housing to its original configuration. In turn, the volume of the interior region returns to the original volume. During this expansion of the interior region, air from the cabin is directed through opening 22 to interior region 20 until the pressure within the interior region reaches equilibrium with ambient. The next time that the submarine dives, the cycle will begin to repeat. This cycle will continue until the fluid is depleted.

Embodiments, other than those specifically described for illustrative purposes only, are envisioned which include means that cause a pressure difference between the interior region of the housing and the area surrounding the housing. Inasmuch as the difference in pressure between the interior region of housing and the region surrounding the housing is related to the temperature and to the volume of the interior region, changes to the volume, pressure or temperature of either of the interior region of the housing or the region surrounding the housing can cause a pressure difference therebetween.

Figure 8:
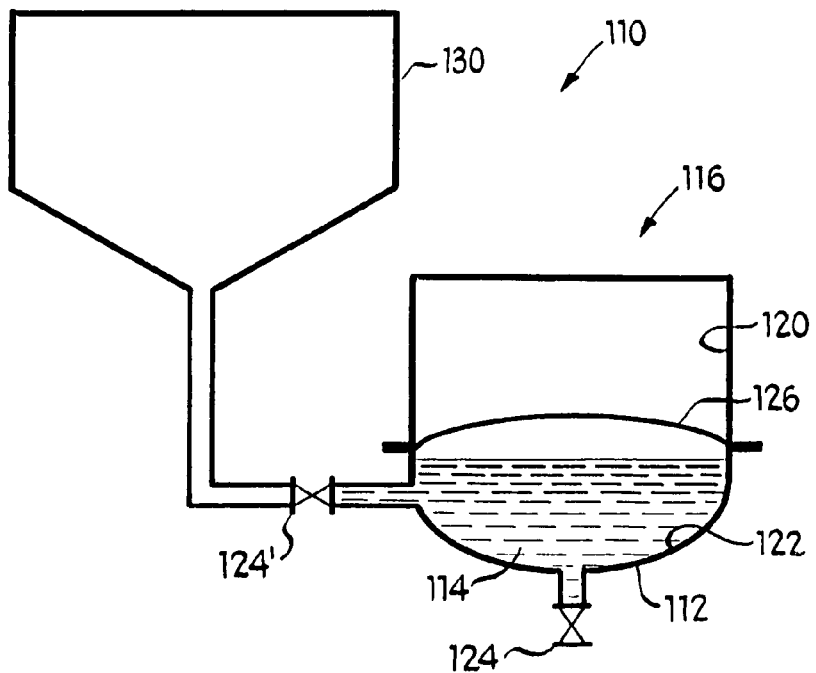
FIG. 8 is a schematic representation of a preferred embodiment of the controlled substance release device.
Figure 9:
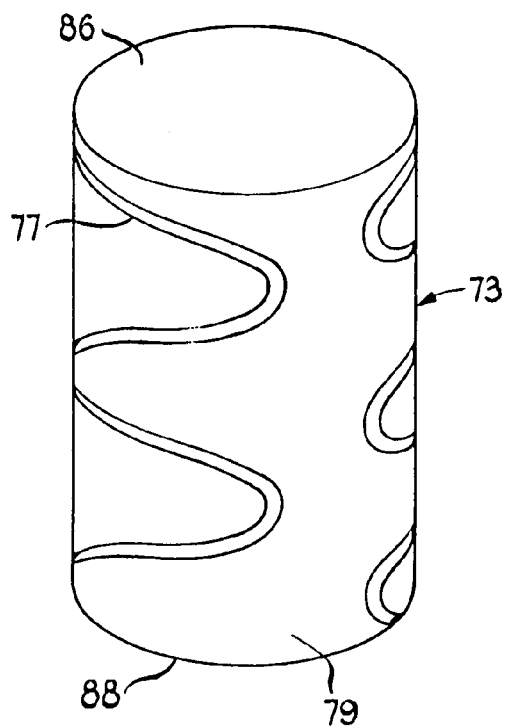
FIG. 9 is a perspective view of another embodiment of the restrictor plug.
Figure 11:
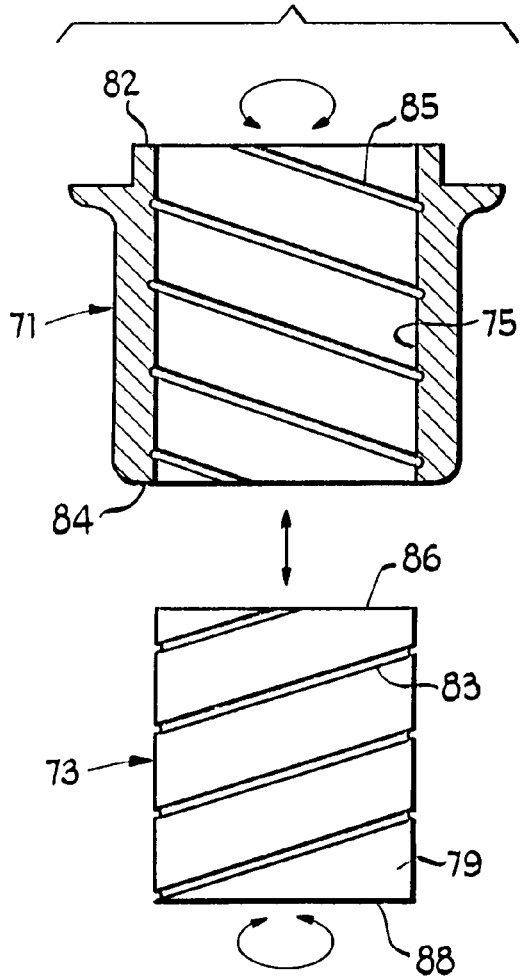
FIG. 11 is a front exploded view of another embodiment of the opening.
Figure 10:
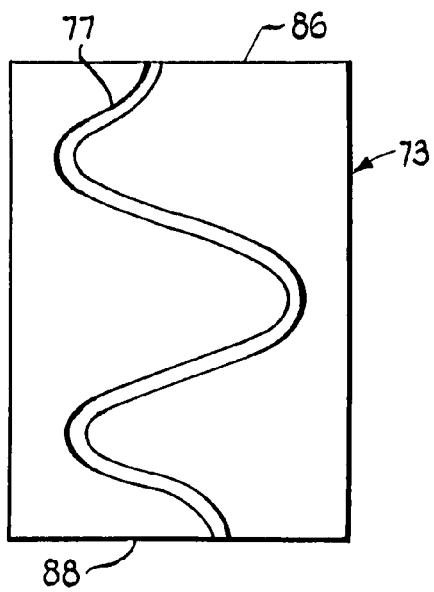
FIG. 10 is a front elevational view of the embodiment of the restrictor plug shown in FIG. 9.

For example, another preferred embodiment of control substance release device 110 is shown in FIG. 8 as comprising housing 112, fluid 114 and means 116 for causing a pressure differential between ambient and the interior of the housing. In particular, housing 112 includes hermetically sealed fixed volume gas chamber 120, fixed volume fluid chamber 122, fluid control valve 124 (check valve) and flexible diaphragm 126 operatively separating the fluid chamber and the gas chamber. These elements generally provide a means for releasing a predetermined quantity of fluid therefrom. In addition, and as will be explained, fluid reservoir 130 is operatively associated with fixed volume fluid chamber 122. As can be seen, another fluid control valve 124' is positioned where the fluid reservoir feeds into the fixed volume fluid chamber. In another embodiment, flexible diaphragm may comprise a slidably adjustable sealing member which provides a means to selectively alter the volume of the housing.

In operation, fluid, originally retained in fluid reservoir 130, passes through fluid control valve 124' and enters into fixed volume fluid chamber 122. When the fluid chamber's volume is substantially occupied by fluid, no more fluid will be allowed to enter the chamber. Inasmuch as fluid reservoir 130 will be vented to atmosphere, flow of fluid will be relatively unrestricted.

As ambient temperature increases or ambient barometric pressure decreases, relative to the gas occupying fixed volume gas chamber 120, the gas in the chamber begins to expand. As the gas continues to expand, it exerts a pushing force on flexible diaphragm 126, which, in turn, exerts a pressure on the fluid within fixed volume fluid chamber 122. As the fluid starts to displace, fluid control valve 124' closes (as a result of the force exerted thereon by the fluid in the fixed volume fluid chamber) and fluid control valve 124, located at the bottom of fixed volume fluid chamber 122 becomes forced open. As a result, the fluid occupying the fixed volume fluid chamber is operatively released therefrom. Preferably, housing 112 is configured so that the minimum temperature and/or pressure change expected in a cycle will be sufficient to dispense the entire contents of the fluid occupying the fixed volume fluid chamber.

As the gas in fixed volume gas chamber 120 contracts, due to a reversal in the pressure differential (caused by a decrease in ambient temperature or an increase in ambient barometric pressure), fluid control valve 124' closes and fluid control valve 124 opens. As a result, fluid, from fluid reservoir 130, is again allowed to fill fixed volume fluid chamber 122 wherein the fluid dispensing cycle can be repeated. Although not shown, it is contemplated that fluid reservoir 130 includes a removable portion so that it can be refilled with fluid as desired.

The foregoing description and drawings merely explain and illustrate the invention and the invention is not limited thereto except insofar as the appended claims are so limited, as those skilled in the art who have the present disclosure before them will be able to make modifications and variations therein without departing from the scope of the invention.

What is claimed is:

1. A device for delivering a fluid comprising:
   a housing having an interior region and an opening, wherein the interior region comprises an interior pressure;
   a quantity of fluid within the interior of housing; and
   means associated with the opening for controlling flow of the quantity of fluid through the opening,
   wherein the housing comprises means for absorbing radiative heat to, in turn, increase the temperature of the quantity of fluid, and the interior pressure, and deliver at least a portion of the quantity of fluid from the housing, and
   further includes means for cyclically varying the pressure differential between the interior region of the housing and the immediate surroundings of the housing.

2. The device according to claim 1 wherein the device further includes a check valve, to, in turn, prevent inadvertent flow of fluid when the interior pressure exceeds a predetermined value.

3. The device according to claim 1 wherein the flow control means further comprises a porous plug.

4. The device according to claim 1, wherein the flow control means further comprises a tunnel of predetermined length and cross-sectional area, so as to permit a certain level of maximum flow therethrough.

5. The device according to claim 4 wherein the opening includes:
   a restrictor plug having an outer surface;
   a receptacle having an inner surface; and
   a groove disposed on one of the inner and outer surfaces,
   wherein the tunnel is defined by the cooperation of the groove and the outer surface upon positioning of the restrictor plug and the receptacle into operative engagement.

6. The device according to claim 1, further comprising an emanator associated with the opening of the housing.

7. The device according to claim 6 wherein the emanator is positioned at a predetermined distance from the opening of the housing.

8. The device according to claim 6 wherein the emanator comprises a porous material.

9. The device according to claim 6 wherein the emanator comprises a substantially non-porous material.

10. The device according to claim 6 wherein the emanator further includes means for enhancing the volatilization of the fluid.

11. The device according to claim 6 wherein the volatilization enhancing means further comprises a ventilation fan associated with the emanator.

12. The device according to claim 6 wherein the volatilization enhancing means further comprises a heating element associated with at least one of the emanator or the housing.

13. The device according to claim 1 further including means for providing a bolus to, in turn, temporarily increase the quantity of fluid delivered from the device.

14. The device according to claim 13 wherein the bolus providing means comprises means for increasing the pressure within the housing, to, in turn, increase flow through the opening.

15. The device according to claim 13 wherein the bolus providing means further comprises:
   a second opening associated with the housing; and
   means for delivering the fluid within the housing through the opening.

16. The device according to claim 15 wherein the delivering means comprises a spray pump.

17. The device according to claim 15 wherein the delivering means comprises an atomizer.

18. The device according to claim 13 wherein the bolus providing means further includes means for enhancing the volatilization of the fluid.

19. The device according to claim 18 wherein the volatilization enhancing means comprises a heating element.

20. The device according to claim 18 wherein the volatilization enhancing means comprises a ventilation fan.

21. A device for delivering a fluid comprising:
   a housing having an interior region and an opening, wherein the interior region comprises an interior pressure;
   a quantity of fluid within the interior of housing; and
   means associated with the opening for controlling flow of the quantity of fluid through the opening,
   the flow control means further comprising a tunnel of predetermined length and cross-sectional area, so as to permit a certain level of maximum flow therethrough, the opening including:
   a restrictor plug having an outer surface;
   a receptacle having an inner surface; and
   a groove disposed on one of the inner and outer surfaces,
   such that the tunnel is defined by the cooperation of the groove and the outer surface upon positioning of the restrictor plug and the receptacle into operative engagement;
   wherein the housing comprises means for absorbing radiative heat to, in turn, increase the temperature of the quantity of fluid, and the interior pressure, and deliver at least a portion of the quantity of fluid from the housing.

22. The device according to claim 21 wherein the pressure differential causing means further includes means for cyclically varying the pressure differential between the interior of the housing and the immediate surroundings of the housing.

23. The device according to claim 22 wherein the bolus providing means further comprises:
   a second opening associated with the housing; and
   means for delivering the fluid within the housing through the opening.

24. The device according to claim 23 wherein the delivering means comprises a spray pump.

25. The device according to claim 23 wherein the delivering means comprises an atomizer.

26. The device according to claim 22 wherein the bolus providing means further includes means for enhancing the volatilization of the fluid.

27. The device according to claim 26 wherein the volatilization enhancing means comprises a heating element.

28. The device according to claim 26 wherein the volatilization enhancing means comprises a ventilation fan.

29. The device according to claim 21 wherein the device further includes a check valve to, in turn, prevent inadvertent flow of fluid when the interior pressure exceeds a predetermined value.

30. The device according to claim 21 wherein the flow control means further comprises a porous plug.

31. The device according to claim 21, further comprising an emanator associated with the opening of the housing.

32. The device according to claim 31 wherein the emanator is positioned at a predetermined distance from the opening of the housing.

33. The device according to claim 31 wherein the emanator comprises a porous material.

34. The device according to claim 31 wherein the emanator comprises a substantially non-porous material.

35. The device according to claim 31 wherein the emanator further includes means for enhancing the volatilization of the fluid.

36. The device according to claim 35 wherein the volatilization enhancing means further comprises a ventilation fan associated with the emanator.

37. The device according to claim 35 wherein the volatilization enhancing means further comprises a heating element associated with at least one of the emanator or the housing.

38. The device according to claim 21 further including means for providing a bolus to, in turn, temporarily increase the quantity of fluid delivered from the device.

39. The device according to claim 38 wherein the bolus providing means comprises means for increasing the pressure within the housing, to, in turn, increase flow through the opening.

40. A device for delivering a fluid comprising:
- a housing having an interior region and an opening, wherein the interior region comprises an interior pressure;
- a quantity of fluid within the interior of housing; and
- means associated with the opening for controlling flow of the quantity of fluid through the opening,
- wherein the housing comprises means for absorbing radiative heat to, in turn, increase the temperature of the quantity of fluid, and the interior pressure, and deliver at least a portion of the quantity of fluid from the housing, and
- further comprising an emanator associated with the opening of the housing.

41. The device according to claim 40 wherein the emanator is positioned at a predetermined distance from the opening of the housing.

42. The device according to claim 40 wherein the emanator comprises a porous material.

43. The device according to claim 40 wherein the emanator comprises a substantially non-porous material.

44. The device according to claim 40 wherein the emanator further includes means for enhancing the volatilization of the fluid.

45. The device according to claim 40 wherein the volatilization enhancing means further comprises a ventilation fan associated with the emanator.

46. The device according to claim 40 wherein the volatilization enhancing means further comprises a heating element associated with at least one of the emanator or the housing.

47. The device according to claim 40 wherein the pressure differential causing means further includes means for cyclically varying the pressure differential between the interior of the housing and the immediate surroundings of the housing.

48. The device according to claim 40 wherein the device further includes a check valve to, in turn, prevent inadvertent flow of fluid when the interior pressure exceeds a predetermined value.

49. The device according to claim 40 wherein the flow control means further comprises a porous plug.

50. The device according to claim 40 wherein the flow control means further comprises a tunnel of predetermined length and cross-sectional area, so as to permit a certain level of maximum flow therethrough.

51. The device according to claim 50 wherein the opening includes:
- a restrictor plug having an outer surface;
- a receptacle having an inner surface; and
- a groove disposed on one of the inner and outer surfaces, wherein the tunnel is defined by the cooperation of the groove and the outer surface upon positioning of the restrictor plug and the receptacle into operative engagement.

52. The device according to claim 40 further including means for providing a bolus to, in turn, temporarily increase the quantity of fluid delivered from the device.

53. The device according to claim 52 wherein the bolus providing means comprises means for increasing the pressure within the housing, to, in turn, increase flow through the opening.

54. The device according to claim 53 wherein the bolus providing means further comprises:
- a second opening associated with the housing; and
- means for delivering the fluid within the housing through the opening.

55. The device according to claim 54 wherein the delivering means comprises a spray pump.

56. The device according to claim 55 wherein the delivering means comprises an atomizer.

57. The device according to claim 53 wherein the bolus providing means further includes means for enhancing the volatilization of the fluid.

58. The device according to claim 57 wherein the volatilization enhancing means comprises a heating element.

59. The device according to claim 58 wherein the volatilization enhancing means comprises a ventilation fan.

60. A device for delivering a fluid comprising:
- a housing having an interior region and an opening, wherein the interior region comprises an interior pressure;
- a quantity of fluid within the interior of housing; and
- means associated with the opening for controlling flow of the quantity of fluid through the opening,
- wherein the housing comprises means for absorbing radiative heat to, in turn, increase the temperature of the quantity of fluid, and the interior pressure, and deliver at least a portion of the quantity of fluid from the housing, and
- further including means for providing a bolus, to, in turn, temporarily increase the quantity of fluid delivered from the device.

61. The device according to claim 60 wherein the bolus providing means comprises means for increasing the pressure within the housing, to, in turn, increase flow through the opening.

62. The device according to claim 60 wherein the bolus providing means further comprises:
 a second opening associated with the housing; and
 means for delivering the fluid within the housing through the opening.

63. The device according to claim 62 wherein the delivering means comprises a spray pump.

64. The device according to claim 62 wherein the delivering means comprises an atomizer.

65. The device according to claim 60 wherein the bolus providing means further includes means for enhancing the volatilization of the fluid.

66. The device according to claim 65 wherein the volatilization enhancing means comprises a heating element.

67. The device according to claim 60 wherein the volatilization enhancing means comprises a ventilation fan.

68. The device according to claim 60 wherein the pressure differential causing means further includes means for cyclically varying the pressure differential between the interior of the housing and the immediate surroundings of the housing.

69. The device according to claim 60 wherein the device further includes a check valve, to, in turn, prevent inadvertent flow of fluid when the interior pressure exceeds a predetermined value.

70. The device according to claim 60 wherein the flow control means further comprises a porous plug.

71. The device according to claim 60 wherein the flow control means further comprises a tunnel of predetermined length and cross-sectional area, so as to permit a certain level of maximum flow therethrough.

72. The device according to claim 71 wherein the opening includes:
 a restrictor plug having an outer surface;
 a receptacle having an inner surface; and
 a groove disposed on one of the inner and outer surfaces, wherein the tunnel is defined by the cooperation of the groove and the outer surface upon positioning of the restrictor plug and the receptacle into operative engagement.

73. The device according to claim 60 further comprising an emanator associated with the opening of the housing.

74. The device according to claim 73 wherein the emanator is positioned at a predetermined distance from the opening of the housing.

75. The device according to claim 74 wherein the emanator comprises a porous material.

76. The device according to claim 74 wherein the emanator comprises a substantially non-porous material.

77. The device according to claim 74 wherein the emanator further includes means for enhancing the volatilization of the fluid.

78. The device according to claim 77 wherein the volatilization enhancing means further comprises a ventilation fan associated with the emanator.

79. The device according to claim 78 wherein the volatilization enhancing means further comprises a heating element associated with at least one of the emanator or the housing.

* * * * *